US012797603B2

(12) United States Patent
Kudlik et al.

(10) Patent No.: US 12,797,603 B2
(45) **Date of Patent: *Nov. 17, 2026**

(54) SPEED CHANGE ALGORITHM TO RESOLVE SUCTION CONDITIONS IN LVADS

(71) Applicant: Medtronic, Inc., Minneapolis, MN (US)

(72) Inventors: D'Anne E. Kudlik, Saint Louis Park, MN (US); Carlos Reyes, Davie, FL (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

This patent is subject to a terminal disclaimer.

(21) Appl. No.: 18/812,538

(22) Filed: Aug. 22, 2024

(65) Prior Publication Data

US 2025/0050092 A1 Feb. 13, 2025

Related U.S. Application Data

(63) Continuation of application No. 16/795,929, filed on Feb. 20, 2020, now Pat. No. 12,090,315.

(51) Int. Cl.

| | |
|---|---|
| ***A61M 60/50*** | (2021.01) |
| ***A61M 60/122*** | (2021.01) |
| ***A61M 60/40*** | (2021.01) |

(52) U.S. Cl.

CPC .......... *A61M 60/50* (2021.01); *A61M 60/122* (2021.01); *A61M 60/40* (2021.01); *A61M 2205/3331* (2013.01); *A61M 2205/3365* (2013.01); *A61M 2205/50* (2013.01)

(58) Field of Classification Search
None
See application file for complete search history.

(56) References Cited

U.S. PATENT DOCUMENTS

| | | | |
|---|---|---|---|
| 7,997,854 | B2 | 8/2011 | LaRose et al. |
| 8,007,254 | B2 | 8/2011 | LaRose et al. |
| 8,419,609 | B2 | 4/2013 | Shambaugh, Jr. et al. |
| 8,506,471 | B2 | 8/2013 | Bourque |
| 8,512,013 | B2 | 8/2013 | LaRose et al. |

(Continued)

OTHER PUBLICATIONS

International Search Report and Written Opinion dated Apr. 14, 2021, for corresponding International Application No. PCT/US2021/016002; International Filing Date: Feb. 1, 2021 consisting of 9 pages.

(Continued)

*Primary Examiner* — Manolis Pahakis

(74) *Attorney, Agent, or Firm* — Shumaker & Sieffert, P.A.

(57) ABSTRACT

A controller for an implantable blood pump, the implantable blood pump having an impeller. The controller includes processing circuitry configured to reduce a speed of the impeller from a set speed to a first reduced speed if a first predetermined amount of time of detected suction events occurs during a first time interval and increase the speed of the impeller from the first reduced speed if a second predetermined amount of time or less of detected suction events occur during a second time interval and a third predetermined amount of time or less of detected suction events.

20 Claims, 3 Drawing Sheets

(56) References Cited

U.S. PATENT DOCUMENTS

| | | | | |
|---|---|---|---|---|
| 8,961,388 | B2 | 2/2015 | Bourque | |
| 9,427,508 | B2 | 8/2016 | Reyes et al. | |
| 9,492,601 | B2 * | 11/2016 | Casas | A61M 60/546 |
| 9,561,313 | B2 | 2/2017 | Taskin | |
| 9,801,988 | B2 | 10/2017 | Bourque | |
| 10,077,777 | B2 | 9/2018 | Horvath et al. | |
| 12,090,315 | B2 * | 9/2024 | Kudlik | A61M 60/122 |
| 2003/0199727 | A1 * | 10/2003 | Burke | A61M 60/216 600/16 |
| 2004/0047736 | A1 * | 3/2004 | Nose | A61M 60/104 417/44.1 |
| 2004/0215050 | A1 | 10/2004 | Morello | |
| 2006/0241335 | A1 | 10/2006 | Benkowski et al. | |
| 2009/0005632 | A1 * | 1/2009 | Schima | A61M 60/178 600/16 |
| 2012/0078031 | A1 * | 3/2012 | Burke | A61M 60/183 600/16 |
| 2013/0338559 | A1 * | 12/2013 | Franano | A61M 60/422 604/4.01 |
| 2014/0100413 | A1 * | 4/2014 | Casas | A61M 60/178 600/16 |
| 2014/0323796 | A1 | 10/2014 | Medvedev et al. | |
| 2015/0306290 | A1 * | 10/2015 | Rosenberg | A61B 5/0215 600/16 |
| 2015/0367048 | A1 | 12/2015 | Brown et al. | |
| 2016/0058929 | A1 | 3/2016 | Medvedev et al. | |
| 2016/0058930 | A1 | 3/2016 | Medvedev et al. | |
| 2017/0185054 | A1 | 6/2017 | Rudser | |
| 2018/0028738 | A1 * | 2/2018 | Brown | A61M 60/419 |
| 2018/0078159 | A1 | 3/2018 | Edelman et al. | |
| 2019/0307938 | A1 * | 10/2019 | Reyes | A61M 60/148 |
| 2019/0351116 | A1 * | 11/2019 | Kudlik | A61M 60/546 |
| 2021/0260263 | A1 | 8/2021 | Kudlik et al. | |

OTHER PUBLICATIONS

Prosecution History from U.S. Appl. No. 16/795,929, dated Oct. 10, 2023 through May 22, 2024, 48 pp.

* cited by examiner

SPEED CHANGE ALGORITHM TO RESOLVE SUCTION CONDITIONS IN LVADS

CROSS-REFERENCE TO RELATED APPLICATION

This application is a continuation of U.S. patent application Ser. No. 16/795,929, filed 20 Feb. 2020, which issued as U.S. Pat. No. 12,090,315 on 17 Sep. 2024, the entire contents of which are incorporated herein by reference.

FIELD

The present technology is generally related to method and controller for operating an implantable blood pump to resolve suction.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta.

If a VAD is operated at a flow rate in excess of an inflow rate of blood to the ventricle, the VAD will create a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline. If the flow rate through the pump is insufficient, the device will not provide sufficient circulatory assistance to the patient. Excessive flow also can create undesirable conditions.

SUMMARY

The techniques of this disclosure generally relate to a method and controller for operating an implantable blood pump to resolve suction.

In one aspect, the present disclosure provides a controller for an implantable blood pump, the implantable blood pump having an impeller. The controller includes processing circuitry configured to reduce a speed of the impeller from a set speed to a first reduced speed if a first predetermined amount of time of detected suction events occurs during a first time interval and increase the speed of the impeller from the first reduced speed if a second predetermined amount of time or less of detected suction events occur during a second time interval and a third predetermined amount of time or less of detected suction events occur during a period of time immediately prior to a speed increase.

In another aspect of this embodiment, the first predetermined amount of time is five seconds and the first time interval is five seconds.

In another aspect of this embodiment, the first predetermined amount of time is six seconds and the first time interval is 10 seconds.

In another aspect of this embodiment, the first predetermined amount of time is seven seconds and the first time interval is 15 seconds.

In another aspect of this embodiment, the first predetermined amount of time is eight seconds and the first time interval is 20 seconds.

In another aspect of this embodiment, the second predetermined amount of time is five seconds and the second time interval is 60 seconds.

In another aspect of this embodiment, the period of time immediately prior to a speed increase is 10 seconds.

In another aspect of this embodiment, the first reduced speed of the impeller is at least 40 rpm less than the set speed.

In another aspect of this embodiment, the processing circuitry is further configured to reduce a speed of the impeller from the first reduced speed to a second reduced speed if the first predetermined amount of time of detected suction events occurs during the first time interval following a reduction of speed from the set speed to the first reduced speed.

In another aspect of this embodiment, the second reduced set speed is at least 40 rpm less than the first reduced set speed.

In another aspect of this embodiment, the implantable blood pump includes a minimum response speed, and wherein the first reduced speed and any subsequent reduction in speed is greater than or equal to the minimum response speed.

In another embodiment, a method of controlling operating of an implantable blood pump, the implantable blood pump having an impeller, includes reducing a speed of the impeller from a set speed to a first reduced speed if a first predetermined amount of time of detected suction events occurs during a first time interval and increasing the speed of the impeller from the first reduced speed if a second predetermined amount of time or less of detected suction events occur during a second time interval and a third predetermined amount of time or less of detected suction events occur during a period of time immediately prior to a speed increase.

In another aspect of this embodiment, the first predetermined amount of time is five seconds and the first time interval is five seconds.

In another aspect of this embodiment, the first predetermined amount of time is six seconds and the first time interval is 10 seconds.

In another aspect of this embodiment, the first predetermined amount of time is seven seconds and the first time interval is 15 seconds.

In another aspect of this embodiment, the first predetermined amount of time is eight seconds and the first time interval is 20 seconds.

In another aspect of this embodiment, the second predetermined amount of time is five seconds and the second time interval is 60 seconds.

In another aspect of this embodiment, the period of time immediately prior to a speed increase is 10 seconds.

In another aspect of this embodiment, the method further includes reducing a speed of the impeller from the first reduced speed to a second reduced speed if the first predetermined amount of time of detected suction events occurs during the first time interval following a reduction of speed from the set speed to the first reduced speed.

In another embodiment, a controller for an implantable blood pump, the implantable blood pump having an impeller, includes processing circuitry configured to reduce a speed of the impeller from a set speed to a first reduced speed if a first predetermined amount of time of detected suction events occurs during a first time interval and increase the speed of the impeller from the first reduced speed if five seconds or less of detected suction events occurs during a 60 second interval and zero seconds of detected suction events occur during a 10 second period time immediately prior to a speed increase and reduce a speed of the impeller from the first reduced speed to a second reduced speed if the first predetermined amount of time of detected suction events occurs during the first time interval following a reduction of speed from the set speed to the first reduced speed.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
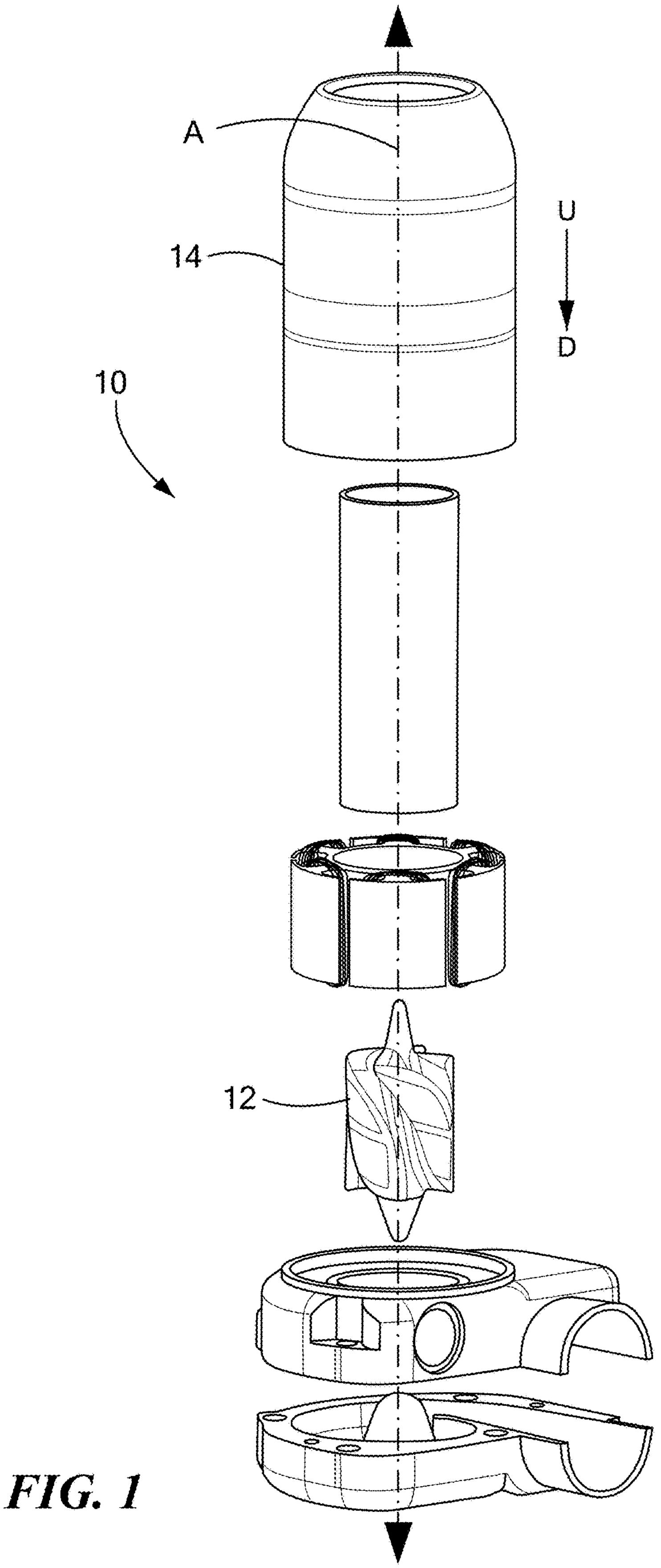
FIG. 1 is a disassembled view of an implantable blood pump.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® Pump or the MVAD® Pump, having a movable element, such as an impeller 12 or a rotor, configured to rotate and impel blood from the heart to the rest of the body. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
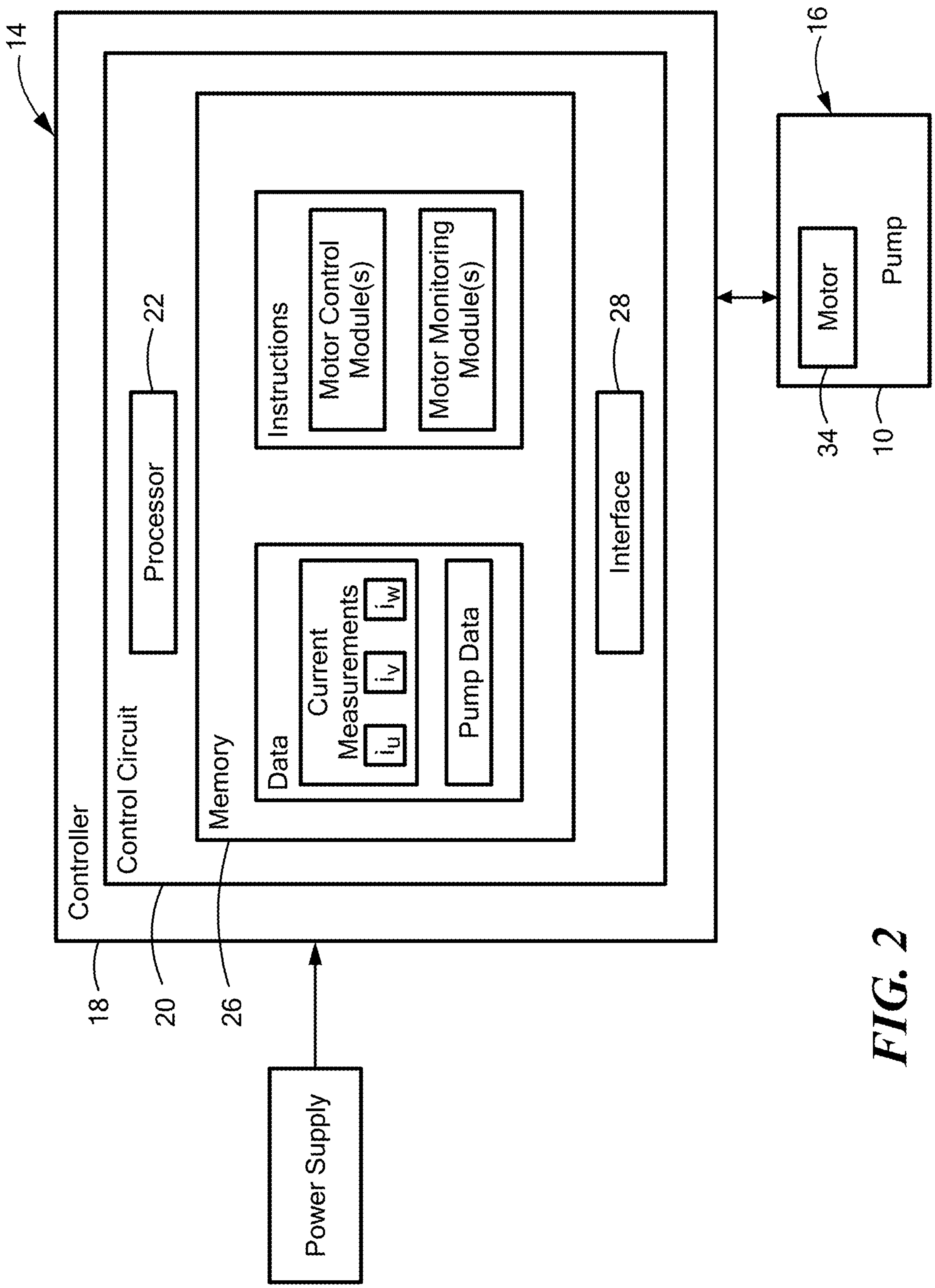
FIG. 2 is a block diagram of a system for controlling a pump speed of the blood pump of FIG. 1.

FIG. 2 is a block diagram of an exemplary system 14 for controlling a pump speed and/or other operations of the implantable blood pump 10 when the blood pump 10 is in communication with the system 14. The blood pump 10 includes a motor 16 therein and may be a separate component or form part of the system 14. In one example, the system 14 includes a controller 18 having a control circuit 20 and a processor 22 including processing circuitry 24 configured to perform the operations of the blood pump 10. The system 14 may also include a memory 26 and an interface 28, the memory 26 being configured to store information accessible by the processor 22, including instructions executable by the processing circuitry 24 and/or data that may be retrieved, manipulated or stored by the processor 22. Such instructions and/or data include that which is used to control the pump speed.

Figure 3:
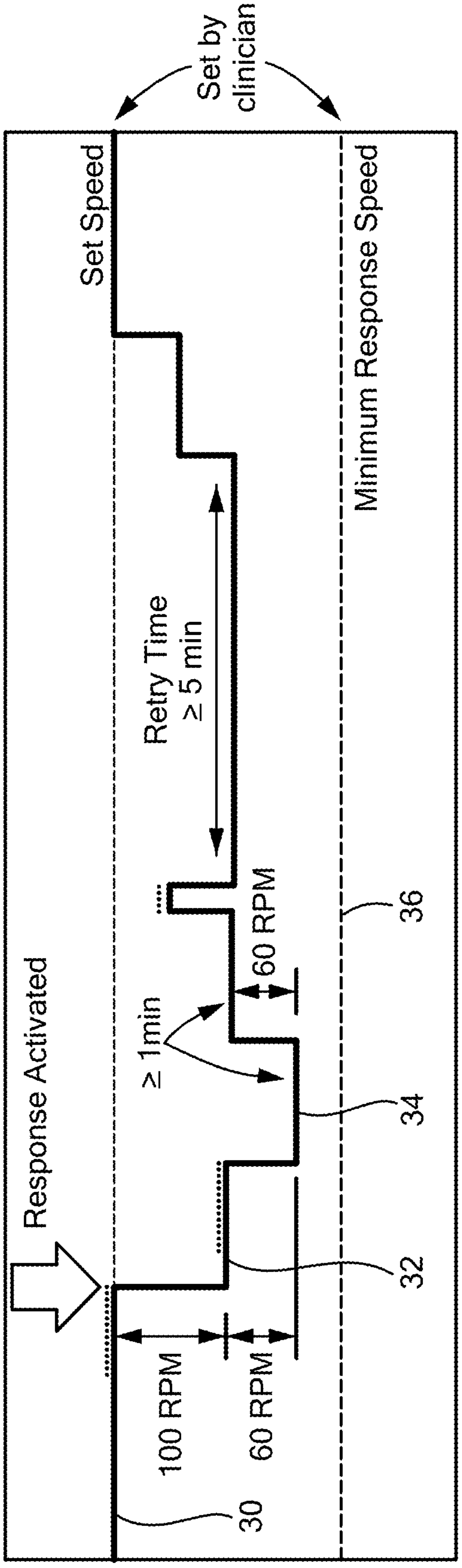
FIG. 3 is a graph showing speed changes for reducing suction.

Referring now to FIG. 3, the processing circuitry 24 may be configured to implement a speed response algorithm in response to detected suction events. Suction events may be detected by, including but not limited to, the methods described in U.S. Pat. No. 9,492,601 and U.S. Patent Publication Number 2018/0028738, the entireties of which are expressly incorporated by reference herein. The severity of the suction events may also be detected by the suction detection algorithm, which may be integrated into the speed response algorithm. In an exemplary configuration, under normal circumstances the pump 10 operates and a pump set speed 30, for example, 2800 RPM. The processing circuitry 24 is configured to reduce a speed of the impeller 12 from the set speed 30 to a first reduced speed 32 if a first predetermined amount of time of detected suction events occurs during a first time interval. In particular, there are several triggers for the reduction of the speed of the impeller 12 from the set speed 30 that are summarized below. If any of the below events occur, the processing circuitry 24 may reduce the speed of the impeller 12 by a predetermined amount to a first reduced speed 32.

The triggers for a reduction in speed include, but are not limited to, five seconds detected in five seconds; or six seconds detected in ten seconds; or seven seconds detected in fifteen seconds; or eight seconds detected in twenty seconds. That is, for example, the first predetermined amount of time of detection suction events may be five seconds and the first time interval may be five seconds, and so on. The reduction of the speed of the impeller 12 from the set speed 30 may be instantaneous or ramped down from the set speed 30 when any one of the triggers are met. If suction events are still detected following a speed decrease, a further reduction in speed may be initiated by the processing circuitry 24 from the first reduced speed 32 if the above triggers are met. For example, if after a reduction of the impeller 12 speed from the set speed 30, for example, 2800 RPM, to the first reduced speed 32, for example, 2700 RPM the suction triggers discussed above are met, a further reduction in speed may be initiated by the processing circuitry 24 to a second reduced speed 34 less than the first reduced speed 32. In one configuration, the second reduction in speed, and any further reductions in speed, is less than or equal to the first reduction in speed. For example, whereas the first reduced speed may be anywhere from a 40 RPM-200 RPM less than the set speed 30, the second reduced speed may be, for example, 40 RPM-60 RPM less than the first reduced speed, but still above a minimum response speed 36 set by the clinician to maintain blood flow through the pump 10. Regardless of suction conditions, the processing circuitry 24 does not reduce the speed of the impeller 12 below the minimum response speed 36 which is the absolute lower boundary for a speed of the impeller 12. For example, if the set speed 30 is 60 RPM above the minimum response speed 36, the speed response algorithm may only reduce the speed of the pump by 60 RPM to the minimum response speed 36, which is the absolute floor for reducing the speed of the pump during the speed response algorithm.

In addition to reducing the speed of the pump base on a predetermined amount of time of one-second suction events, the processing circuitry may trigger a reduction in speed from the set speed 30 if suction is detected during a predetermined number of cardiac cycles in which suction is detected. For example, and without limitation, if suction is detected during 5 cardiac cycles out of 10 cardiac cycles, the speed response algorithm may be initiated. Moreover, in one configuration, the speed response algorithm may also be configured to trigger a reduction in speed based on suction being detected over a combination of a predetermined amount of time and a predetermined number of cardiac cycles. For example, and without limitation if suction is detected during 3 cardiac cycles and for 10 seconds, the speed of the pump may be reduced. Additionally, because the severity of suction may also be detected, the more severe the suction the more sensitive the speed reduction algorithm may be. For example, if mild suction is detected, the speed response algorithm may be triggered after a longer predetermined period of time, whereas more severe suction may trigger and immediate initiation of the speed response algorithm. Thus, the speed response algorithm can assign a rating to the severity of the suction, whether mild, moderate, or severe, and initiate a speed reduction algorithm based on the rating.

The processing circuitry 24 may further be configured to increase the speed of the impeller 12 from the second reduced speed 34 or the first reduced speed 32. If a second predetermined amount of time or less of detected suction events occur in second time interval, or predetermined number of cardiac cycles, and a third predetermined amount of time or less of detected suction events occur during a period of time immediately prior to a speed increase, then a speed of the impeller 12 may be increased. If such conditions are not met, the speed of the impeller 12 may be maintained at either the first reduced speed 32 or the second reduced speed 34. For example, if less than five seconds of suction is detected in sixty seconds and zero seconds of suction is detected in the last ten seconds, then the speed may be increased from, for example, the second reduced speed 34 to the first reduced speed 32. If while attempting to increase the speed from any of the reduced speeds triggers are met, the speed of the impeller 12 may be reduced back to the prior speed and the processing circuitry may delay in trying to increase the speed of the impeller 12. For example, as shown in FIG. 3, a delay of 5 minutes may be implemented by the processing circuitry in which the speed of the impeller 12 may be maintained at a reduced speed before further attempts to increase the speed of the impeller are attempted.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A blood pump system comprising:

a blood pump comprising an impeller configured to cause blood to flow in a patient; and a controller communicatively coupled to the blood pump and comprising processing circuitry configured to:

reduce a speed of the impeller from a set speed to a first reduced speed in response to determining that a first predetermined amount of time of detected suction events occurred during a first time interval prior to the reduction of the speed of the impeller from the set speed to the first reduced speed; and increase the speed of the impeller from the first reduced speed in response to determining that a second predetermined amount of time or less of detected suction events occurred during a second time interval and a third predetermined amount of time or less of detected suction events occurred during a third time interval after the reduction of the speed of the impeller from the set speed to the first reduced speed and prior to the increase of the speed of the impeller, wherein a start of the third time interval occurs after a start of the second time interval, wherein the second time interval and the third time interval occur after the first time interval and after the reduction of the speed, and the second predetermined amount of time or less of detected suction events and the third predetermined amount of time or less of detected suction events are different.

2. The blood pump system of claim 1, wherein the processing circuitry is further configured to reduce the speed of the impeller from the first reduced speed to a second reduced speed in response to the first predetermined amount of time of detected suction events occurring during the first time interval following a reduction of speed from the set speed to the first reduced speed.

3. The blood pump system of claim 2, wherein the second reduced speed is at least 40 revolutions per minute (RPM) less than the first reduced speed.

4. The blood pump system of claim 1, wherein the blood pump is configured to operate at a minimum response speed, and wherein the first reduced speed and any subsequent reduction in speed is greater than or equal to the minimum response speed.

5. The blood pump system of claim 1, wherein the processing circuitry is further configured to maintain the speed of the impeller at the first reduced speed in response to determining that more than the second predetermined amount of time of detected suction events occurred during the second time interval or determining that more than the third predetermined amount of time of detected suction events occurred during the third time interval.

6. The blood pump system of claim 1, wherein the blood pump comprises a ventricular assist device.

7. The blood pump system of claim 1, wherein the first reduced speed of the impeller is 40-200 revolutions per minute (RPM) less than the set speed.

8. The blood pump system of claim 1, wherein the processing circuitry is further configured to delay attempting to increase the speed of the impeller from the first reduced speed for a retry time in response to determining that more than the second predetermined amount of time of detected suction events occurred during the second time interval or more than the third predetermined amount of time of detected suction events occurred during the third time interval after the reduction of the speed of the impeller from the set speed to the first reduced speed and prior to the increase of the speed of the impeller, wherein a start of the third time interval occurs after a start of the second time interval.

9. The blood pump system of claim 8, wherein the retry time is greater than or equal to five minutes.

10. The blood pump system of claim 1, wherein the second time interval is greater than one minute.

11. A method of controlling an impeller of a blood pump, the method comprising:

determining that a first predetermined amount of time of detected suction events occurred during a first time interval;

reducing a speed of the impeller from a set speed to a first reduced speed in response to determining that the first predetermined amount of time of the detected suction events occurred during the first time interval, wherein the first time interval is prior to the reduction of the speed of the impeller from the set speed to the first reduced speed;

determining that a second predetermined amount of time or less of detected suction events occurred during a second time interval after the reduction of the speed of the impeller from the set speed to the first reduced speed;

determining a third predetermined amount of time or less of detected suction events occurred during a third time interval after the reduction of the speed of the impeller from the set speed to the first reduced speed; and increasing the speed of the impeller from the first reduced speed in response to determining that the second predetermined amount of time or less of detected suction events occurred during the second time interval and determining that the third predetermined amount of time or less of detected suction events occurred during the third time interval, wherein a start of the third time interval occurs after a start of the second time interval, wherein the second time interval and the third time interval occur after the first time interval and after reducing the speed, and the second predetermined amount of time or less of detected suction events and the third predetermined amount of time or less of detected suction events are different.

12. The method of claim 11, further comprising:

reducing the speed of the impeller from the first reduced speed to a second reduced speed in response to the first predetermined amount of time of detected suction events occurring during the first time interval following a reduction of speed from the set speed to the first reduced speed.

13. The method of claim 12, wherein the second reduced speed is at least 40 revolutions per minute (RPM) less than the first reduced speed.

14. The method of claim 11, wherein the blood pump is configured to operate at a minimum response speed, and wherein the first reduced speed and any subsequent reduction in speed is greater than or equal to the minimum response speed.

15. The method of claim 11, further comprising:

maintaining the speed of the impeller at the first reduced speed in response to determining that more than the second predetermined amount of time of detected suction events occurred during the second time interval or determining that more than the third predetermined amount of time of detected suction events occurred during the third time interval.

16. The method of claim 11, wherein the blood pump comprises a ventricular assist device.

17. The method of claim 11, wherein the first reduced speed of the impeller is 40-200 revolutions per minute (RPM) less than the set speed.

18. The method of claim 11, further comprising:

delaying attempting to increase the speed of the impeller from the first reduced speed for a retry time in response to determining that more than the second predetermined amount of time of detected suction events occurred during the second time interval or more than the third predetermined amount of time of detected suction events occurred during the third time interval after the reduction of the speed of the impeller from the set speed to the first reduced speed and prior to the increase of the speed of the impeller, wherein a start of the third time interval occurs after a start of the second time interval.

19. The method of claim 18, wherein the retry time is greater than or equal to five minutes.

20. The method of claim 11, wherein the second time interval is greater than one minute.

* * * * *